US00PP27806P3

(12) United States Plant Patent
van der Zwet

(10) Patent No.: US PP27,806 P3
(45) Date of Patent: Mar. 21, 2017

(54) *CAMPANULA* PLANT NAMED 'CHICO LILA'

(50) Latin Name: *Campanula glomerata*
Varietal Denomination: Chico Lila

(71) Applicant: Alexius Joannes Joseph van der Zwet, Oude-Wetering (NL)

(72) Inventor: Alexius Joannes Joseph van der Zwet, Oude-Wetering (NL)

(73) Assignee: Green Elite Collection B.V., Lisserbroek (NL)

( * ) Notice: Subject to any disclaimer, the term of this patent is extended or adjusted under 35 U.S.C. 154(b) by 0 days.

(21) Appl. No.: 14/756,086

(22) Filed: Jul. 29, 2015

(65) Prior Publication Data

US 2017/0034979 P1 Feb. 2, 2017

(51) Int. Cl.
*A01H 5/02* (2006.01)

(52) U.S. Cl.
USPC ..... Plt./414

(58) Field of Classification Search
USPC ..... Plt./414
See application file for complete search history.

(56) References Cited

PUBLICATIONS

UPOV hit on *Campanula* Plant named 'Chico Lila', CA PBR 14-8493, published Jan. 31, 2016.*
UPOV hit on *Campanula* Plant named 'Chico Lila', QZ PBR 20150397, published Apr. 15, 2015.*

* cited by examiner

*Primary Examiner* — Anne Grunberg
(74) *Attorney, Agent, or Firm* — C. A. Whealy

(57) ABSTRACT

A new and distinct *Campanula* plant named 'Chico Lila', characterized by its compact and upright plant habit; strong stems; freely flowering habit; lilac-colored flowers; and relatively long flowering period.

3 Drawing Sheets

Botanical designation: *Campanula glomerata.*
Cultivar denomination: 'CHICO LILA'.

CROSS-REFERENCED TO CLOSELY-RELATED APPLICATION

Title: *Campanula* Plant Named 'Chantal'.
Applicant: Alexius Joannes Joseph van der Zwet
Filed: Concurrently with this application having application Ser. No. 14/756,082

BACKGROUND OF THE INVENTION

The present invention relates to a new and distinct *Campanula* plant, botanically known as *Campanula glomerata* and hereinafter referred to by the cultivar name 'Chico Lila'.

The new *Campanula* plant is a product of a planned breeding program conducted by the Inventor in Oude-Wetering, The Netherlands. The objective of the breeding program is to create new freely-flowering *Campanula* plants that flower for a long period of time.

The new *Campanula* plant originated from an open-pollination during the summer of 2007 of an unnamed selection of *Campanula glomerata*, not patented, as the female, or seed, parent with an unknown selection of *Campanula glomerata*, as the male, or pollen, parent. The new *Campanula* plant was discovered and selected by the Inventor as a single flowering plant from within the progeny of the stated open-pollination grown in a controlled environment in Oude-Wetering, The Netherlands in June, 2009.

Asexual reproduction of the new *Campanula* plant by divisions a controlled environment in Oude-Wetering, The Netherlands, since August, 2009, has shown that the unique features of the new *Campanula* plant are stable and reproduced true to type in successive generations.

SUMMARY OF THE INVENTION

Plants of the new *Campanula* plant have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Chico Lila'. These characteristics in combination distinguish 'Chico Lila' as a new and distinct *Campanula* plant:

1. Compact and upright plant habit.
2. Strong stems.
3. Freely flowering habit.
4. Lilac-colored flowers.
5. Relatively long flowering period.

Plants of the new *Campanula* differ from plants of the female parent selection primarily in plant size as plants of the new *Campanula* are more compact than plants of the female parent selection.

Plants of the new *Campanula* differ from plants of 'Chantal', disclosed in a U.S. Plant Patent application filed concurrently having application Ser. No. 14/756,082, in the following characteristics:

1. Petals of flowers of plants of the new *Campanula* are not fused at the apices whereas petals of flowers of plants of 'Chantal' are fused at the apices.

2. Plants of the new *Campanula* and 'Chantal' differ in flower color as plants of 'Chantal' have light purple-colored flowers.

Plants of the new *Campanula* can be compared to plants of *Campanula glomerata* 'Emerald', disclosed in U.S. Plant Pat. No. 18,343. In side-by-side comparisons conducted by the Inventor in Oude-Wetering, The Netherlands, plants of the new *Campanula* differed primarily from plants of 'Emerald' in the following characteristics:

1. Plants of the new *Campanula* were more compact than plants of 'Emerald'.
2. Plants of the new *Campanula* had shorter and stronger stems than plants of 'Emerald'.
3. Plants of the new *Campanula* and 'Emerald' differed in flower color as plants of 'Emerald' had light purple-colored flowers.

Plants of the new *Campanula* can also be compared to plants of *Campanula* 'Caroline', not patented. In side-by-side comparisons conducted by the Inventor in Oude-Wetering, The Netherlands, plants of the new *Campanula* differed primarily from plants of 'Caroline' in the following characteristics:

1. Plants of the new *Campanula* were more compact than plants of 'Caroline'.
2. Plants of the new *Campanula* had shorter and stronger stems than plants of 'Caroline'.
3. Plants of the new *Campanula* and 'Caroline' differed in flower color as plants of 'Caroline' had pinkish purple-colored flowers.

BRIEF DESCRIPTION OF THE PHOTOGRAPHS

The accompanying colored photographs illustrate the overall appearance of the new *Campanula* plant showing the colors as true as it is reasonably possible to obtain in colored reproductions of this type. Colors in the photographs may differ slightly from the color values cited in the detailed botanical description which accurately describe the actual colors of the new *Campanula* plant.

The photograph on the first sheet is a side perspective view of a typical flowering plant of 'Chico Lila' grown in a container.

The photograph on the second sheet is a close-up view of a typical leaf of 'Chico Lila'.

The photograph on the third sheet is a close-up view of a typical flowering plant of 'Chico Lila'.

DETAILED BOTANICAL DESCRIPTION

Plants used for the aforementioned photographs and following description were grown in 24-cm containers during the spring in a glass-covered greenhouse in Oude-Wetering, The Netherlands and under cultural practices typical of commercial *Campanula* production. During the production of the plants, day temperatures ranged from 13° C. to 27° C. and night temperatures ranged from 5° C. to 18° C. Plants were one year old when the photographs and description were taken. In the following description, color references are made to The Royal Horticultural Society Colour Chart, 2007 Edition, except where general terms of ordinary dictionary significance are used.

Botanical classification: *Campanula glomerata* 'Chico Lila'.

Parentage:

*Female parent*.—Unnamed selection of *Campanula glomerata*, not patented.

*Male parent*.—Unknown selection of *Campanula glomerata*, not patented.

Propagation:

*Type*.—By divisions.

*Root description*.—Medium in thickness, fibrous; typically white in color, actual color of the roots is dependent on substrate composition, water quality, fertilizers, substrate temperature and physiological age of roots.

*Rooting habit*.—Freely branching; dense.

Plant description:

*Plant and growth habit*.—Herbaceous perennial; compact and upright plant form; inverted triangle; low vigor to moderately vigorous growth habit; campanulate flowers arranged in terminal and axillary clusters.

*Plant height*.—About 28 cm.

*Plant width*.—About 23.8 cm.

*Branch description*.—Branching habit: Basal branching habit with numerous basal branches developing per plant in subsequent years of growth. Length: About 23.5 cm. Diameter: About 1.1 cm. Internode length: About 1.7 cm. Strength: Strong. Aspect: Upright to about 5° from vertical. Texture: Densely pubescent. Luster: Slightly glossy. Color: Close to 144A strongly tinged with close to N186C.

Leaf description:

*Arrangement*.—Alternate, simple.

*Length*.—About 8.1 cm.

*Width*.—About 4.4 cm.

*Shape*.—Ovate.

*Apex*.—Acute.

*Base*.—Cordate or attenuate.

*Margin*.—Finely serrate.

*Texture, upper and lower surfaces*.—Moderately rugose, rough; moderately pubescent.

*Luster, upper and lower surfaces*.—Slightly glossy.

*Venation pattern*.—Pinnate.

*Color*.—Developing leaves, upper surface: Close to 137B to 137C. Developing leaves, lower surface: Close to 147B. Fully expanded leaves, upper surface: Close to between N137A and 139A; venation, close to 147B. Fully expanded leaves, lower surface: Close to 147B; venation, close to 147D.

*Petioles*.—Stem leaves are sessile; basal leaves are petiolate. Length: About 4 cm. Diameter: About 2 mm by 3 mm. Strength: Strong. Texture, upper and lower surfaces: Pubescent. Color, upper and lower surfaces: Close to 146B; margins, close to N137A.

Flower description:

*Flower arrangement and flowering habit*.—Single campanulate flowers arranged in terminal and axillary clusters; flowers face mostly upright to slightly outwardly; freely flowering habit with about 37 flowers developing in terminal clusters and about 14 flowers developing in axillary clusters.

*Natural flowering season*.—Plants begin flowering about nine months after planting; relatively long flowering period, plants flower continuously from mid-June to early August in The Netherlands.

*Flower longevity on the plant*.—About ten days; flowers persistent.

*Fragrance*.—None detected.

*Flower buds*.—Length: About 2.5 cm. Diameter: About 1.5 cm. Shape: Narrowly oblong. Color: Proximally, close to 148D; distally, close to between N187C and 187D.

*Flower cluster height*.—About 5.7 cm.

*Flower cluster diameter*.—About 9 cm.

*Flower diameter*.—About 3.1 cm.

*Flower depth* (*height*).—About 3.6 cm.

*Petals*.—Quantity and arrangement: Typically five in a single whorl; fused toward the lower half of the petal. Length: About 3.2 cm. Width: About 9 mm. Shape: Narrowly obovate. Apex: Acute. Margin: Entire. Texture, upper surface: Smooth, glabrous. Texture, lower surface: Pubescent. Luster, upper and lower surfaces: Slightly glossy. Color: When opening, upper surface: Close to 85C; towards the apex, close to 70B. When opening, lower surface: Close to between 84C and 85C, closest to 85C. Fully opened, upper surface: Close to 85B to 85C; mid-section, slightly tinged with close to N88D; towards the apex, close to 70B; color does not fade with development. Fully opened, lower surface: Close to 85B to 85C; towards the apex, close to 84C; color does not fade with development.

*Sepals*.—Quantity and arrangement: Typically five in a single whorl; fused towards the base. Length: About 1.5 cm. Width: About 4 mm. Shape: Lanceolate. Apex: Narrowly acute. Margin: Entire. Texture, upper and lower surfaces: Moderately pubescent. Luster, upper and lower surfaces: Matte. Color: When opening and fully opened, upper surface: Close to 143A; towards the margins, close to N137A. When opening and fully opened, lower surface: Close to 143A; towards the margins, close to N137A.

*Peduncles*.—Length: About 4.1 cm. Diameter: About 7 mm. Aspect, flowers in terminal clusters: Mostly upright. Aspect, flowers in axillary clusters: About 30° from branch axis. Strength: Strong. Texture: Smooth, glabrous. Color: Close to 144C strongly tinged with close to N186C.

*Reproductive organs*.—Stamens: Quantity per flower: Five. Filament length: About 2 mm. Filament color: Close to NN155D. Anther shape: Lanceolate. Anther length: About 7 mm. Anther color: Close to 10B to 10C; at the apex, close to 150B. Pollen amount: Moderate. Pollen color: Close to 4D. Pistils: Quantity per flower: One. Pistil length: About 1.9 cm. Stigma shape: Three-parted, decurrent. Stigma color: Close to 146D. Style length: About 1.7 cm. Style color: Close to 84D. Ovary color: Close to 145A to 145B.

*Seeds and fruits*.—Seed and fruit production has not been observed on plants of the new *Campanula*.

Disease & pest resistance: Plants of the new *Campanula* have not been noted to be resistant to pathogens and pests common to *Campanula* plants.

Garden performance: Plants of the new *Campanula* have exhibited good tolerance to rain and wind, to tolerate high temperatures about 35° C. and to be suitable for USDA Hardiness Zones 3 through 8.

It is claimed:

1. A new and distinct *Campanula* plant named 'Chico Lila' as illustrated and described.

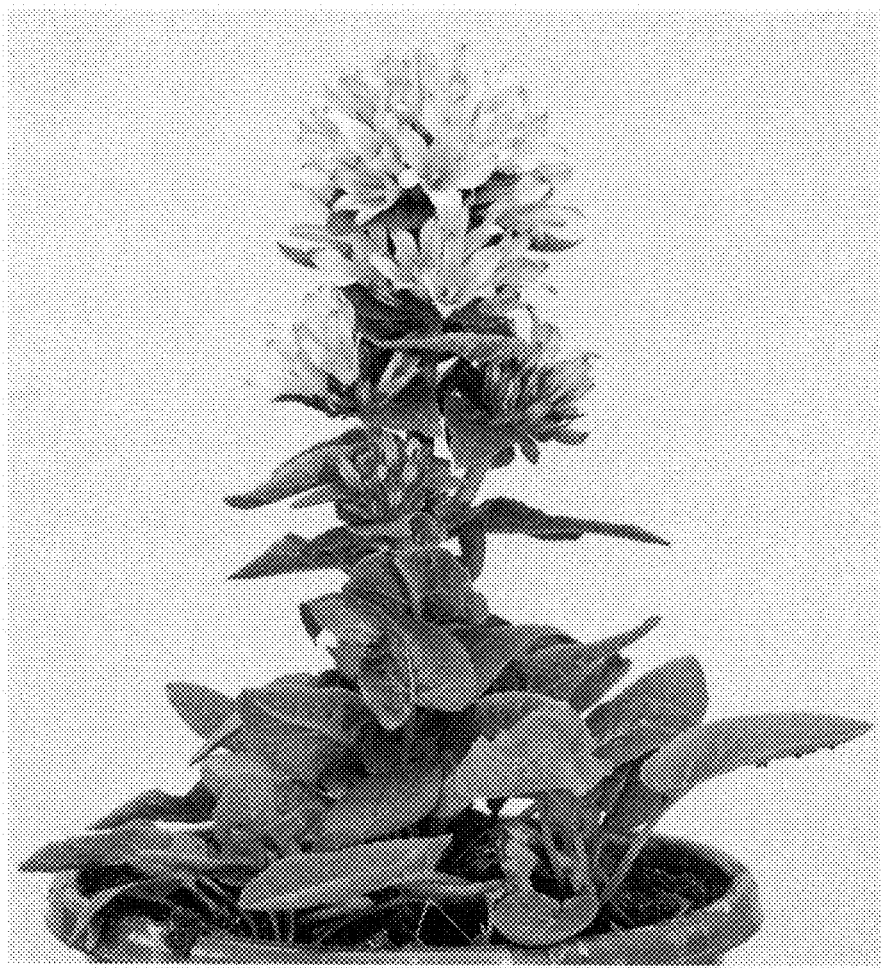

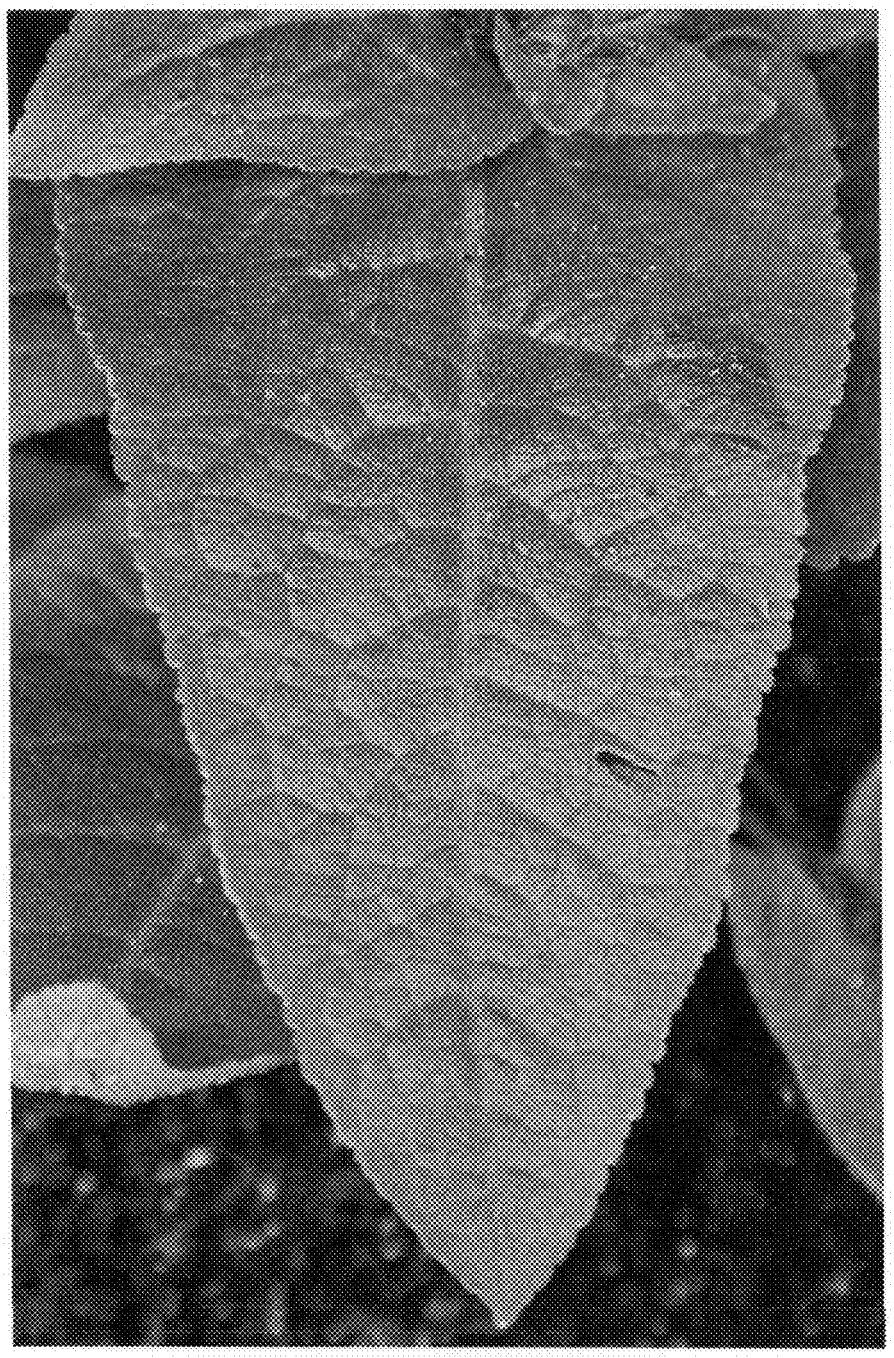

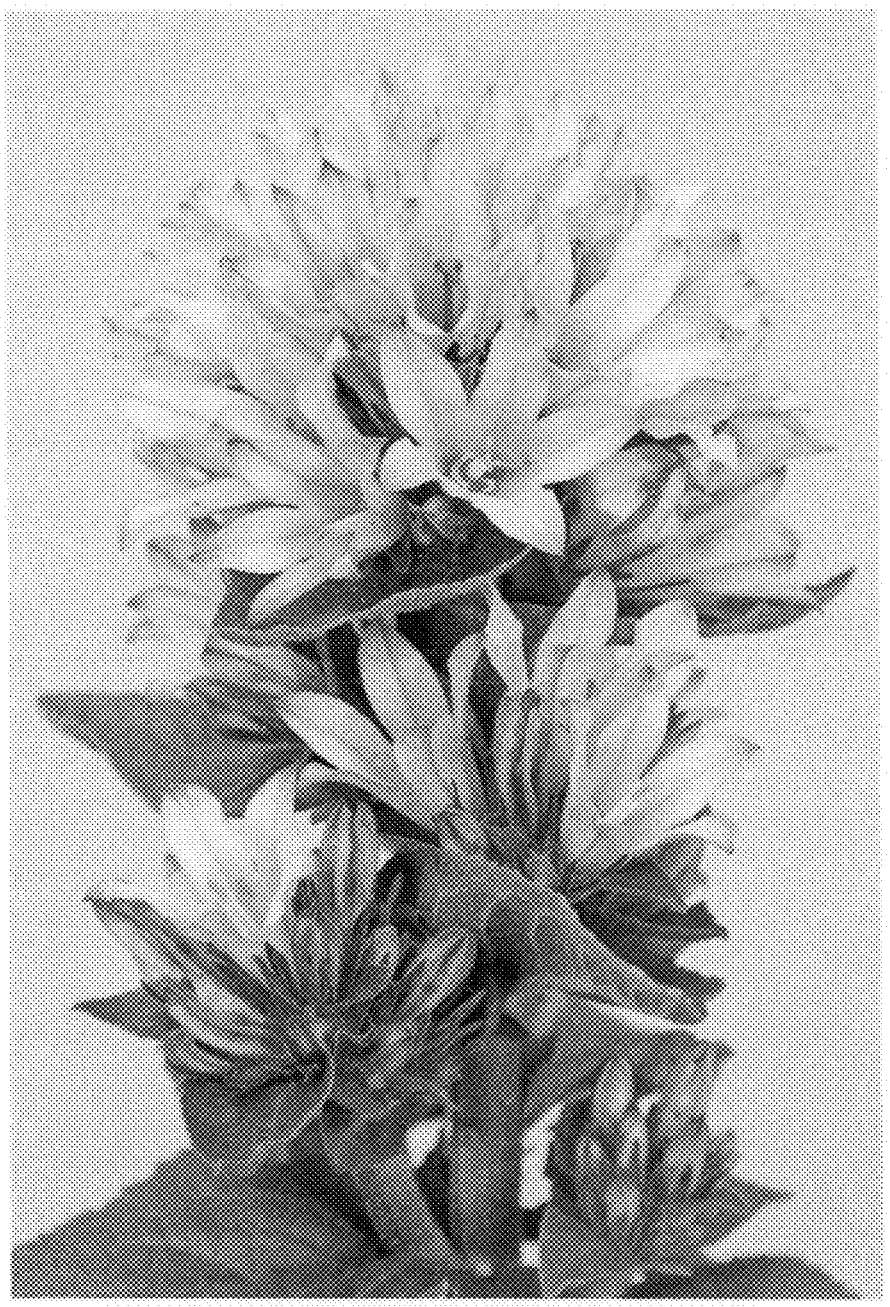

* * * * *